(12) United States Patent
Serrano De Las Heras et al.

(10) Patent No.: US 8,129,336 B1
(45) Date of Patent: Mar. 6, 2012

(54) INHIBITOR OF THE URACIL-DNA GLYCOSYLASE ENZYME AND USES THEREOF

(75) Inventors: Gemma Serrano De Las Heras, Madrid (ES); Alicia Bravo Garcia, Madrid (ES); Margarita Salas Falgueras, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 13/281,953

(22) Filed: Oct. 26, 2011

Related U.S. Application Data

(62) Division of application No. 12/158,871, filed as application No. PCT/ES2006/070187 on Dec. 1, 2006.

(30) Foreign Application Priority Data

Dec. 23, 2005 (ES) .................................. 200503240

(51) Int. Cl.
*A01N 37/18* (2006.01)

(52) U.S. Cl. ......................................... 514/2.3; 514/4.1

(58) Field of Classification Search .................... 514/2.3, 514/4.1
See application file for complete search history.

(56) References Cited

OTHER PUBLICATIONS

Heras et al., "Protein p56 from the *Bacillus subtilis* phage Φ29 inhibits DNA-binding ability of uracil-DNA glycosylase." vol. 35, No. 16. Nucleic Acids Research, 2007.
Sambrook et al., Molecular cloning, a Laboratory Manual, Cold Sprint Harbor Laboratory Press 1989; 2nd ed. vol. 1-3 sections 1.53-16.40.
Bravo et al., Initiation of Bacteriophage 029 DNA Replication in Vivo: Assembly of a Membrane-associated Multiprotein Complex, J. Mol. Biol. (1997) 269:102-112.
Studier et al., Use of Bacteriophage T7 RNA Polumerase to Direct Selective High-level Expression of Cloned Genes, J. Mol, Biol. (1986) 189:113-130.
Moreno et al., Suppressor-Sensitive Mutants and Genetic map of *Bacillus subtilis* Bacteriophage Ø29, Virology 62, 1-16 (1974).
Trillo, Tratado de Farmacia Galenica, Luzan 5, S.A. de Ediciones 1993; 1$^{st}$ Edition Italian.
Perkins, et al., Probability-based protein identification by searching sequence databases using mass spectrometry data, Electrophoresis (1999) 20: 3551-3567.
Yoshikawa et al., Nucleotide sequence of the major early region of bacteriophage Ø29, Gene(1982) 17:323-335.
Studebaker et al., Depletion of uracil-DNA glycosylase activity is associated with decreased cell proliferation, Biochemical and Biophysical Research Communications, (2005), vol. 334, pp. 509-515.
Wang et al., Uracil-DNA Glycosylase Inhibitor Gene of Bacteriophage PBS2 Encodes a Binding Protein Specific for Uracil-DNA Glycosylase, The Journal of Biological Chemistry, (1989), vol. 264, No. 2, pp. 1163-1171.
Schagger et al., Tricine-Sodium Dodecyl Sulfate-Polyacrylamide Gel Electrophoresis for the Separation of Proteins in the Range from 1 to 100 kDa, Analytical Biochemistry, (1987) 166: 368-379.
Paces et al., Uniprot Database, accession No. P06498, Jan 1988.

*Primary Examiner* — Maryam Monshipouri
(74) *Attorney, Agent, or Firm* — Leason Ellis LLP

(57) ABSTRACT

The present invention relates to a protein which has the capacity to bind to and inhibit the viral uracil DNA glycosylase (UDG) enzyme and its use as a therapeutic agent; in particular, as an antiviral agent.

1 Claim, 2 Drawing Sheets

INHIBITOR OF THE URACIL-DNA GLYCOSYLASE ENZYME AND USES THEREOF

This application is a divisional of U.S. patent application Ser. No. 12/158,871 filed Sep. 12, 2008 entitled "Inhibitor of the Uracil-DNA Glycosylase Enzyme and Uses Thereof, pending" which is a U.S. national phase application under 35 U.S.C. §371 of the International Patent Application No. PCT/ES2006/070187 filed Dec. 1, 2006, which claims the benefit of priority to Spanish Patent Application No. P200503240 filed Dec. 23, 2005, the disclosures of all of which are hereby incorporated by reference in their entireties. The International Application was published in Spanish on Jul. 5, 2007 as WO 2007/074200.

FIELD OF THE INVENTION

This invention relates to a protein that inhibits the viral uracil DNA glycosylase (UDG) enzyme and the use thereof as a therapeutic agent, in particular, as an antiviral agent.

BACKGROUND OF THE INVENTION

Viral infections in persons and animals, especially in persons, are widely spread and pose numerous problems for healthcare workers. Pharmaceutical agents capable of effectively and specifically fighting viruses are very limited in number and, moreover, generally cause undesirable secondary effects. Viral infections not only destroy host cells, but also affect the functioning of various proteins and enzymes. Viral invasion favours infection by other pathogenic agents, such as other viruses, bacteria, fungi, etc. Thus, for example, due to the immune loss which it causes, the human immunodeficiency virus (HIV) opens the door to other viruses (herpes simplex, cytomegalovirus, hepatitis B virus) and other pathogenic agents that invade the human body, creating dangerous situations.

Despite intense efforts, thus far it has not been possible to find chemotherapeutic agents which interfere, with an essentially recognisable success, either at the origin or in terms of the symptoms, with the pathogenic episodes caused by viral agents. Therefore, the treatment of viral diseases by chemotherapeutic agents is still incomplete.

Antibody conjugates, formed by a conjugated or hybrid monoclonal antibody and a toxin, have been used to eradicate specific colonies of target cells, directing them against "undesired" target cells that carry surface target antigens and destroying them. The various toxins that have been used by different researchers may be broadly classified into two groups. The first group consists of intact toxins, such as intact ricin. These toxins may not be safely applied in vivo due to their lethal toxicity. The toxins in the second group are called hemitoxins. Hemitoxins are single-strand ribosome-inactivating proteins which act catalytically on eukaryotic ribosomes and inactivate the 60S subunit, leading to a dose-dependent inhibition of the synthesis of cell proteins at the peptide elongation level.

A hemitoxin of interest is the pokeweed antiviral protein (PAP), which is isolated from *Phytolacca americana*. For many years, it has been recognised that PAP has antiviral activity. It has been demonstrated that PAP blocks the transmission of RNA-containing viruses in plants. It has also been reported that PAP inhibits the replication of two RNA-containing animal viruses: poliovirus and influenza virus, and that PAP inhibits the multiplication of simple herpes viruses type I and type II (U.S. Pat. No. 4,672,053). Although it has been reported that PAP monoclonal antibody conjugates G3.7/CD7, F13/CD14 and B43/CD19 inhibit the replication of HIV-1, these conjugates have turned out to be inconsistent in their capacity to inhibit the replication of the viruses.

In light of the above, the need remains to provide new antiviral compounds or drugs. Advantageously, these new antiviral agents should exhibit an efficacy that is equal to or greater than that of the antiviral agents disclosed in the state of the art and should not cause undesirable secondary effects.

Most prokaryotic and eukaryotic cells encode the uracil DNA glycosylase (UDG) enzyme. The function of this enzyme is to eliminate the uracil residues that appear in DNA due to cytosine deamination or to the incorrect incorporation of dUMP during the replication process. For example, if cytosine deamination occurs and it is not repaired, a C-to-T transition mutation will occur in the DNA strand wherein said deamination has taken place and, consequently, a G-to-A transition mutation will take place in the complementary strand after the next replication round. Once the uracil is eliminated by the UDG enzyme, an apurinic or apyrimidinic site (AP site) is created. The mechanism in charge of repairing these AP sites is the base-splicing repair pathway.

In human cells, up to five different enzymes with UDG activity have been identified. Curiously, one of these enzymes, called UNG2, is present in the particles of the type 1 human immunodeficiency virus (HIV-1). Moreover, some DNA viruses, such as herpesviruses and poxviruses, encode their own UDG activity. As a result of the UDG enzyme's capacity to influence the viral replication of different herpesviruses, said enzyme has been associated with the virus replication mechanism in the host cell. In the above-mentioned viruses, it is known that the UDG enzyme is essential for the infective process. It has been proposed that this enzyme's function in viral replication processes is associated with those viruses' capacity to replicate in non-dividing cells, wherein the levels of cellular UDG enzyme are considered to be low (Priet et al. (2005) Mol. Cell. 17: 479-490) and, consequently, the inhibition thereof is of therapeutic interest. Thus far, some inhibitors of the UDG enzyme encoded by simple herpes virus type 1 (SHV-1) have been designed. These non-protein synthetic compounds have been tested in in vitro systems. On the other hand, it is well-known that the UGI protein encoded by the PBS2 bacteriophage inhibits the UDG enzyme of the SHV-1 virus. However, one disadvantage of this inhibitor is that it also blocks the UDG activity of the human UNG2 enzyme.

SUMMARY OF THE INVENTION

This invention is based on the discovery of a protein that has the capacity to inhibit the UDG enzyme. Since the UDG activity of some viruses is essential for the infective process, said protein could be a useful tool to design antiviral compounds.

Therefore, one aspect of the invention relates to a protein that comprises amino acid sequence SEQ ID NO: 1, or a variant or fragment thereof which has the capacity to inhibit the UDG enzyme.

In another aspect, the invention relates to an isolated polynucleotide that encodes said protein.

In another aspect, the invention relates to a gene construct that comprises said polynucleotide.

In another aspect, the invention relates to a vector that comprises said polynucleotide or said gene construct.

In another aspect, the invention relates to a cell that comprises said polynucleotide, or said gene construct, or said vector.

In another aspect, the invention relates to a method of obtaining said protein, which comprises culturing said cell under conditions that allow to produce said protein and, if so desired, recover said protein from the culture medium.

In another aspect, the invention relates to a composition that comprises said protein.

In another aspect, the invention relates to a pharmaceutical composition that comprises said protein, jointly with one or more pharmaceutically acceptable excipients.

In another aspect, the invention relates to the use of said protein in the preparation of an antiviral pharmaceutical composition.

DETAILED DESCRIPTION OF THE INVENTION

Figure 1:
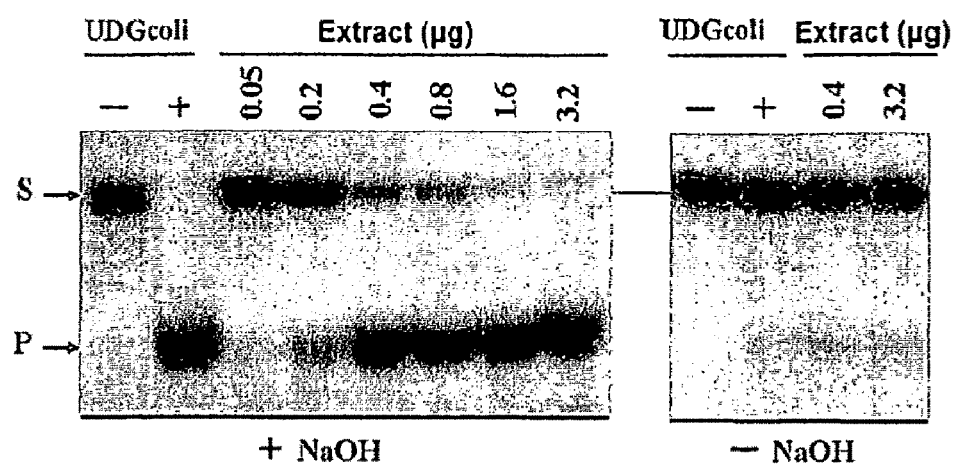
FIG. 1 shows the UDG activity in *B. subtilis* extracts. The radioactively labelled ssDNA-U$^{16}$ substrate (S) (0.55 ng) was incubated with the specified quantity of extract in the absence of Mg$^{2+}$. As an internal control, the substrate was incubated with the UDG enzyme of *E. coli*. The reaction mixtures were treated with NaOH or not. The formation of the splicing product (P) was analysed in polyacrylamide-urea gels.

The invention relates, in general, to a protein with the capacity to inhibit the uracil DNA glycosylase (UDG) enzyme, which comprises amino acid sequence SEQ ID NO: 1, or a variant or fragment thereof that maintains said capacity to inhibit the UDG enzyme, and to its use as a therapeutic agent, in particular, as an antiviral agent.

In one aspect, the invention relates to a protein that comprises amino acid sequence SEQ ID NO: 1, or a variant or fragment thereof with the capacity to inhibit the uracil DNA glycosylase (UDG) enzyme.

For simplicity reasons, the expression "protein of the invention" includes this protein, which comprises amino acid sequence SEQ ID NO: 1, or a variant or fragment thereof with the capacity to inhibit the UDG enzyme. The term "protein", as used herein, includes all forms of post-translational modifications; for example, glycosylation, phosphorylation or acetylation.

In a particular embodiment, the protein of the invention comprises, or is composed of, the amino acid sequence shown in SEQ ID NO: 1 and exhibits, at least, the capacity to bind to said UDG enzyme and inhibit the activity thereof, for which reason it may be used as an antiviral agent. In a specific embodiment, the protein of the invention is the so-called protein p56 of the phi29 (φ29) bacteriophage.

In the sense used in this description, the term "variant" refers to a peptide that is substantially homologous and functionally equivalent to the protein that comprises amino acid sequence SEQ ID NO: 1. As used herein, a peptide is "substantially homologous" to said protein when its amino acid sequence has a degree of identity with respect to the amino acid sequence of said protein of, at least, 60%, advantageously of, at least, 70%, preferably of, at least, 85%, and, more preferably of, at least, 95%. Likewise, the expression "functionally equivalent", as used herein, means that the peptide in question maintains the capacity to inhibit UDG enzyme activity. The capacity to inhibit UDG enzyme activity may be determined by the assay described in Example 1 (see section 1.6 of Materials and Methods); similarly, a peptide's or protein's capacity to bind to the UDG enzyme may be determined by the assay described in Example 1 (see section 1.6 of Materials and Methods).

In a particular embodiment, said variant is a mutant form of the protein that comprises amino acid sequence SEQ ID NO: 1 which maintains the capacity to inhibit UDG enzyme activity. This mutant form may have insertions, deletions or modifications of one or more amino acids with respect to the protein that comprises SEQ ID NO: 1, provided that it preserves the capacity to inhibit UDG enzyme activity.

Illustrative, non-limiting examples of variants included within the scope of this invention include the protein identified in this description as protein p56FLAG, obtained by the modification of gene 56 (which encodes protein p56 of φ29) such that it encodes a p56 protein that contains amino acid sequence DYKDDDDK (FLAG peptide) [SEQ ID NO: 9] fused to the C-terminal end, as described in Example 1 (see section 1.3 of Materials and Methods). By means of affinity chromatography, it has been shown that said protein p56FLAG interacts with the UDG enzyme (see Example 1).

Likewise, in the sense used in this description, the term "fragment" refers to a peptide which comprises a portion of said protein that comprises amino acid sequence SEQ ID NO: 1, that is, a sequence of adjacent amino acids comprised within said SEQ ID NO: 1; to be used in this invention, said fragment must have the capacity to inhibit UDG enzyme activity.

The protein of the invention may be obtained from an organism that produces it, using a method which consists of culturing said organism under suitable conditions for the expression of said protein, and recovering it. In a particular embodiment of this invention, the producing organism is the φ29 bacteriophage. Example 1 discloses the production, isolation and purification of a protein that comprises amino acid sequence SEQ ID NO: 1, specifically, protein p56 of φ29, as well as of a variant thereof (p56FLAG) that has the capacity to bind to the UDG enzyme and inhibit its enzymatic activity.

Additionally, the protein of the invention may be a part of a fusion protein. In this regard, for illustrative, non-limiting purposes, said fusion protein may contain a region A composed of a first peptide that comprises the protein of the invention bound to a region B that comprises a second peptide. Said second peptide may be any appropriate peptide; for example, a peptide with antiviral activity. In a particular embodiment, said second peptide may be a protein of the invention. Said region B may be bound to the amino-terminal region of said region A, or, alternatively, said region B may be bound to the carboxyl-terminal region of said region A. Both regions, A and B, may be bound directly or through a spacer peptide (linker) between said regions A and B. The fusion protein may be obtained by conventional methods known by those skilled in the art; for example, by the gene expression of the nucleotide sequence that encodes said fusion protein in appropriate host cells.

The protein of the invention may be found, if so desired, in a composition that comprises said protein of the invention and an inert vehicle. Said composition constitutes an additional aspect of this invention.

Practically any inert vehicle, that is, one that is not harmful to the protein of the invention, may be used in the preparation of said composition. In a particular embodiment, for illustrative, non-limiting purposes, said composition comprises a protein of the invention and a buffer composed of 50 mM pH 7.5, 1 mM EDTA, 7 mM β-mercaptoethanol and 50% glycerol, suitable to keep the protein of the invention purified at −70° C.

From the information provided by the protein of the invention, the nucleic acid sequence that encodes said protein may be identified and isolated using conventional techniques known by those skilled in the art; for example, by creating genomic libraries of genomic DNA (gDNA) or copy DNA (cDNA) from organisms that produce said protein; designing suitable oligonucleotides to amplify, by polymerase chain reaction (PCR), a region of the genomic clone of the organisms producing said protein which may be used to obtain probes designed to examine said genomic libraries; and analysing and selecting the positive clones.

Therefore, in another aspect, the invention relates to an isolated polynucleotide, hereinafter, polynucleotide of the invention, that encodes said protein of the invention.

In a particular embodiment, the polynucleotide of the invention comprises, or is composed of, the nucleotide sequence shown in SEQ ID NO: 2. In a specific embodiment, the polynucleotide of the invention encodes protein p56 of φ29. Alternatively, the polynucleotide of the invention may exhibit variations in its sequence with respect to nucleotide sequence SEQ ID NO: 2; for example, substitutions, insertions and/or deletions of one or more nucleotides, provided that the resulting polynucleotide encodes a protein of the invention. Therefore, the scope of this invention includes polynucleotides that are substantially homologous to the polynucleotide of SEQ ID NO: 2 and encode a protein of the invention.

In the sense used in this description, a polynucleotide is "substantially homologous" to the polynucleotide of SEQ ID NO: 2 when its nucleotide sequence has a degree of identity with respect to nucleotide sequence SEQ ID NO: 2 of, at least, 60%, advantageously of, at least, 70%, preferably of, at least, 85%, and, more preferably of, at least, 95%. Typically, a polynucleotide that is substantially homologous to the polynucleotide of SEQ ID NO: 2 may be isolated from an organism that produces the protein of the invention on the basis of the information contained in said SEQ ID NO: 2, or is constructed on the basis of the DNA sequence shown in SEQ ID NO: 2; for example, by introducing conservative or non-conservative substitutions. Other examples of possible modifications include the insertion of one or more nucleotides in the sequence, the addition of one or more nucleotides at either end of the sequence, or the deletion of one or more nucleotides at either end or in the interior of the sequence.

In another aspect, the invention relates to a gene construct, hereinafter, gene construct of the invention, that comprises said polynucleotide of the invention.

The gene construct of the invention may incorporate, operatively bound, a sequence that regulates the expression of the polynucleotide of the invention, thus constituting an expression cassette. As used in this description, the expression "operatively bound" means that the protein of the invention, encoded by the polynucleotide of the invention, is expressed within the correct reading frame under the control of the expression control or regulatory sequences.

Control sequences are sequences that control and regulate the transcription and, if applicable, the translation of the protein of the invention, and include promoter sequences, transcriptional regulator encoding sequences, ribosome-binding sequences (RBS) and/or transcription termination sequences. In a particular embodiment, said expression control sequence is functional in prokaryotic cells and organisms; for example, bacteria, etc., whereas, in another particular embodiment, said expression control sequence is functional in eukaryotic cells and organisms; for example, insect cells, vegetable cells, mammal cells, etc. Advantageously, the construct of the invention additionally comprises a marker or gene that encodes a motif or a phenotype which allows for the selection of the host cell transformed by said construct.

The gene construct of the invention may be obtained using techniques that are widely known in the state of the art [Sambrook et al., "Molecular cloning, a Laboratory Manual", 2nd ed., Cold Spring Harbor Laboratory Press, N.Y, 1989 Vol. 1-3].

The gene construct of the invention may be inserted in an appropriate vector. Therefore, in another aspect, the invention relates to a recombinant vector, hereinafter vector of the invention, that comprises the polynucleotide of the invention or the gene construct of the invention. The choice of the vector will depend on the host cell wherein it will be subsequently introduced. In a particular embodiment, the vector of the invention is an expression vector.

For illustrative purposes, the vector wherein said nucleic acid sequence is introduced may be a plasmid, which, when introduced in a host cell, is integrated or not in said cell's genome. Illustrative, non-limiting examples of vectors wherein the polynucleotide of the invention or the gene construct of the invention may be inserted include plasmid pCR2.1-TOPO (expression vector of *E. coli*), marketed by Invitrogen, or plasmid pPR53 (expression vector of *Bacillus subtilis*) (Bravo and Sales (1997) J. Mol. Biol. 269: 102-112).

The vector of the invention may be obtained by conventional methods known by those skilled in the art [Sambrook et al., "Molecular cloning, a Laboratory Manual", 2nd ed., Cold Spring Harbor Laboratory Press, N.Y, 1989 Vol. 1-3]. In a particular embodiment, said vector is a useful vector to transform animal cells.

The vector of the invention may be used to transform, transfect or infect cells that are susceptible to being transformed, transfected or infected by said vector. These cells may be prokaryotic or eukaryotic. The vector of the invention may be used to transform eukaryotic cells, such as yeast cells, for example, *Saccharomyces cerevisiae*, or prokaryotic cells, such as bacteria, for example, *Escherichia coli* or *Bacillus subtilis*. Illustrative, non-limiting examples of cells that are susceptible to being transformed, transfected or infected by the vector of the invention include *E. coli* TOP10 (Invitrogen), *E. coli* BL21 (DE3) (Studier and Moffatt (1986) J. Mol. Biol. 189: 113-130), *B. subtilis* 110NA (Moreno et al. (1974) Virology 62: 1-16) and *B. subtilis* YB886 (Yasbin et al. (1980) Gene 12: 155-159).

Therefore, in another aspect, the invention relates to a host cell, hereinafter cell of the invention, that is transformed, transfected or infected with a vector provided by this invention. The cell of the invention comprises, therefore, a polynucleotide of the invention, a gene construct of the invention, an expression cassette provided by this invention or a vector of the invention, and is capable of expressing the protein of the invention.

The cell of the invention may be a eukaryotic cell, such as a yeast cell, for example, *S. cerevisiae*, or a prokaryotic cell, such as a bacterium, for example, *E. coli* or *B. subtilis*. Illustrative, non-limiting examples of cells that may be used to obtain cells of the invention include *E. coli* TOP10 (Invitrogen), *E. coli* BL21 (DE3) (Studier and Moffatt (1986) J. Mol. Biol. 189: 113-130), *B. subtilis* 110NA (Moreno et al. (1974) Virology 62: 1-16) and *B. subtilis* YB886 (Yasbin et al. (1980) Gene 12: 155-159).

The cells of the invention may be obtained by conventional methods known by those skilled in the art [Sambrook et al., 1989, cited supra[.

In another aspect, the invention relates to a method of obtaining a protein of the invention, which comprises culturing a cell of the invention under conditions that allow to produce said protein and, if so desired, recover said protein from the culture medium. The conditions to optimise the culture of said cell will depend on the cell used. The method of producing the protein of the invention includes, optionally, isolating and purifying said protein of the invention.

As mentioned above, the protein of the invention has the capacity to inhibit the UDG enzyme, for which reason it may be used as a therapeutic agent; in particular, as an antiviral agent.

Therefore, in another aspect, the invention relates to the protein of the invention as a therapeutic agent. In a particular embodiment, the invention relates to the protein of the invention as an antiviral agent.

In general, in order to be administered to a subject, the protein of the invention will be formulated in a pharmaceutical composition. Therefore, in another aspect, the invention relates to a pharmaceutical composition, hereinafter pharmaceutical composition of the invention, that comprises a protein of the invention, jointly with one or more pharmaceutically acceptable excipients.

The term "subject", as used herein, refers to a member of a mammal species, and includes, but is not limited thereto, pets, primates and humans; preferably, the subject is a human being, male or female, of any age or race.

More specifically, in order to be administered to a subject, the protein of the invention will be formulated in a pharmaceutical form suitable to be administered to a subject by any administration route. To this end, the pharmaceutical composition of the invention will include the necessary pharmaceutically acceptable vehicles and excipients to prepare the pharmaceutical form for the selected administration.

The pharmaceutical composition of the invention comprises, at least, a protein of the invention in a therapeutically effective quantity. In the sense used in this description, the expression "therapeutically effective quantity" refers to the quantity of the protein of the invention calculated to produce the desired effect and, in general, will be determined, amongst other causes, by the protein's characteristics and the therapeutic effect to be achieved.

For illustrative purposes, the dose of the protein of the invention to be administered to a subject will be a therapeutically effective quantity and may vary within a broad range. The pharmaceutical composition of the invention may be administered one or more times a day for preventive or therapeutic purposes. The dose of the protein of the invention to be administered will depend on numerous factors, which include the characteristics of the protein of the invention used, such as, for example, its activity and biological half-life, the concentration of the protein of the invention in the pharmaceutical composition, the subject's clinical condition, the severity of the infection or pathology, the pharmaceutical form for the selected administration, etc. For this reason, the doses mentioned in this invention should be considered to be only guides for the person skilled in the art, who must adjust the doses on the basis of the above-mentioned variables.

The pharmaceutical composition of the invention may be formulated in a solid pharmaceutical form, for example (tablets, capsules, pills, granules, suppositories, etc.), or in liquid form (solutions, suspensions, emulsions, etc.) to be administered by any suitable administration route. In a particular embodiment, the pharmaceutical composition of the invention is administered by oral, rectal, topical or parenteral route (e.g., intramuscular, subcutaneous, intravenous, etc.). In each case, the suitable pharmaceutically acceptable excipients for the chosen pharmaceutical form and administration route will be selected.

In a particular embodiment, the protein of the invention will be formulated in a pharmaceutical form suitable for topical administration. Illustrative, non-limiting examples of said pharmaceutical forms include aerosols, solutions, suspensions, emulsions, gels, ointments, creams, dressings, patches, collutories, etc. To this end, the pharmaceutical composition of the invention will include the necessary pharmaceutically acceptable vehicles and excipients to prepare the pharmaceutical form. Information about said vehicles and excipients, as well as about said pharmaceutical forms to administer the protein of the invention may be found in gallenic pharmacy treatises. A review of the different pharmaceutical forms of administering drugs, in general, and of the methods of preparing them may be found in the book "Tratado de Farmacia Galénica", by C. Faulí i Trillo, 1st Edition, 1993, Luzán 5, S.A. de Ediciones.

In another particular embodiment, the protein of the invention will be formulated in a pharmaceutical form suitable for oral administration. In a particular embodiment, said pharmaceutical form for oral administration of the protein of the invention may be solid or liquid. Illustrative, non-limiting examples of suitable pharmaceutical forms to administer the protein of the invention by oral route include tablets, capsules, syrups and solutions, and may contain conventional excipients known in the state of the art, such as binding agents, for example, syrup, acacia, gelatin, sorbitol, tragacanth, polyvinylpyrrolidone, etc.; loads, for example, lactose, sugar, corn starch, calcium phosphate, sorbitol, glycine, etc.; lubricants to prepare tablets, for example, magnesium stearate, etc.; disaggregating agents, for example, starch, polyvinylpyrrolidone, starch sodium glycolate, microcrystalline cellulose, etc.; pharmaceutically acceptable wetting agents, such as sodium lauryl sulfate, etc. Information about said vehicles or excipients, as well as about said pharmaceutical forms to administer the protein of the invention may be found in the book "Tratado de Farmacia Galénica", by C. Faulí i Trillo, 1st Edition, 1993, Luzán 5, S.A. de Ediciones, cited supra.

In another particular embodiment, the protein of the invention will be formulated in a pharmaceutical form suitable for parenteral administration (e.g., intramuscular, subcutaneous, intravenous, etc); for example, in the form of sterile solutions, suspensions or lyophilised products in a suitable unit pharmaceutical form. Suitable excipients may be used, such as buffering agents, surfactants, preservatives, etc. Information about said vehicles or excipients, as well as about said pharmaceutical forms to administer the protein of the invention may be found in the book "Tratado de Farmacia Galénica", by C. Faulí i Trillo, 1st Edition, 1993, Luzán 5, S.A. de Ediciones, cited supra.

The production of said pharmaceutical forms to administer the protein of the invention by any of the selected routes may be performed by conventional methods known by those skilled in the art, such as the habitual methods described or mentioned in the Spanish and US Pharmacopoeias and in similar reference texts. For illustrative purposes, information about the methods of producing said pharmaceutical forms to administer the protein of the invention may be found in the book "Tratado de Farmacia Galénica", by C. Faulí i Trillo, 1st Edition, 1993, Luzán 5, S.A. de Ediciones, cited supra.

In a particular embodiment, the pharmaceutical composition of the invention is used as an antiviral agent, that is, in the treatment and/or prevention of viral infections, such as infections caused by herpesviruses and poxviruses.

The pharmaceutical composition of the invention may be used with other drugs to provide a combination therapy. The other drugs may be a part of the same composition or be supplied as a separate pharmaceutical composition to be administered at the same time (simultaneous administration) as the pharmaceutical composition of the invention or at a different time (sequential administration). In a particular embodiment, said drugs used in combination therapy include antiviral agents.

In another aspect, the invention relates to the use of the protein of the invention in the preparation of an antiviral pharmaceutical composition, that is, in the preparation of a pharmaceutical composition for the treatment and/or prevention of viral infections.

Said antiviral pharmaceutical composition a pharmaceutical composition of the invention and comprises, at least, one protein of the invention, jointly with one or more pharmaceutically acceptable vehicles or excipients.

In a particular embodiment, said antiviral pharmaceutical composition may contain, in addition to a protein of the invention, one or more additional antiviral compounds or drugs, of protein origin or not, in order to increase the effectiveness of the protein of the invention as an antiviral agent, thereby generating a combination therapy. Said additional drugs may be a part of the same pharmaceutical composition or, alternatively, may be supplied in the form of a separate composition to be administered simultaneously or successively (time-sequenced) with respect to the administration of the pharmaceutical composition of the invention.

The following example illustrates the invention and should not be considered to limit the scope thereof.

Example 1

Protein p56 Inhibits UDG Enzyme Activity and, Moreover, Binds Thereto
I. Materials and Methods
1.1 Construction of Plasmid pCR2.1-TOPO.p56

The TOPO TA cloning system developed by Invitrogen was used. Briefly, a DNA region of φ29, containing gene 56, was amplified by the polymerase chain reaction technique (PCR), using the following oligonucleotides as primers:

5'-CGCATTGTATGAGCTTTCTAGGATGG-3' [SEQ ID NO: 3]
5'-GCAGGGAATTCTGCAGTCAAAGGACTTTATC-3' [SEQ ID NO: 4]

In this amplification, Taq DNA polymerase was used, which has the peculiarity of adding a deoxyadenosine residue to the 3' ends of the amplified fragment (267 pb), thereby generating protruding ends. As an inducible expression vector, the linear form of plasmid pCR2.1-TOPO, marketed by Invitrogen, was used; its protruding 3' ends have a deoxythymidine residue and are covalently bound to the DNA topoisomerase I enzyme of the Vaccinia virus. Using this cloning system, digestion with restriction enzymes and the use of DNA ligase are not necessary, since DNA topoisomerase I is responsible for the ligation reaction. Subsequently, the ligation mixture was used to transform the *E. coli* TOP10 strain (Invitrogen). Transformants resistant to kanamycin (50 μg/ml) were selected and the plasmid content was analysed by digestion with restriction enzymes. The recombinant plasmid was called pCR2.1-TOPO.p56. The integrity of gene 56 was confirmed by sequencing.

1.2 Construction of Plasmid pPR53.p56

The 272-pb PstI fragment of plasmid pCR2.1-TOPO.p56, which carries gene 56, was cloned in the PstI site of expression vector pPR53 (Bravo and Salas (1997) J. Mol. Biol. 269: 102-112). For the cloning, the *B. subtilis* YB886 strain was used (Yasbin et al. (1980) Gene 12: 151-159). Transformants resistant to phleomycin (0.8 μg/ml) were selected. The recombinant plasmid was called pPR53.p56. The YB886-[pPR53.p56] strain constitutively produces protein p56.

1.3. Construction of Plasmid pPR53.p56FLAG

The sequence of gene 56 was modified by directed mutagenesis so that it would encode a p56 protein carrying the DYKDDDDK peptide fused to the C-terminal end (protein p56FLAG). The mutagenesis was performed in two steps. First, gene 56 was amplified by PCR using plasmid pPR53.p56 as the template and the following oligonucleotides as primers:

5'-CCTCTAGAGTCGACCTGCAG-3' [SEQ ID NO: 5]
5'-GTCATCGTCATCCTTATAGTCAGGACTT-TATCCAACCTTAG-3' [SEQ ID NO: 6]

In the second step, the 298-pb amplified fragment was used as the template and the oligonucleotides identified as SEQ ID NO: 5 and SEQ ID NO: 7 [5'-CCCTCAGGGCTGCAGT-TATTACTTGTCATCGTCATCCTTATAGTC-3'] were used as primers.

Primer oligonucleotides SEQ ID NO: 5 and SEQ ID NO: 7 carry a recognition sequence for the PstI enzyme. Subsequently, the amplified fragment (322 pb) was digested with the PstI enzyme, and the 293-pb digestion product was cloned in the PstI site of expression vector pPR53 (Bravo and Salas (1997) J. Mol. Biol. 269: 102-112). The ligation mixture was used to transform the *B. subtilis* YB886 strain (Yasbin et al. (1980) Gene 12: 151-159). Transformants resistant to phleomycin (0.8 μg/ml) were selected. The recombinant plasmid was called pPR53.p56FLAG. The YB886-[pPR53.p56FLAG] strain constitutively produces protein p56FLAG. Subsequently, in order to perform in vivo protein-protein interaction studies, plasmid pPR53.p56FLAG was introduced into the *B. subtilis* 110NA strain (Moreno et al. (1974) Virology 62:1-16).

1.4 Purification of Protein p56

Plasmid pCR2.1-TOPO.p56 was introduced into the *E. coli* BL21 (DE3) strain by electroporation techniques. The BL21 (DE3)[pCR2.1-TOPO.p56] strain was grown in kanamycin-containing LB medium (50 μg/ml) at 34° C. When the culture reached an optical density of 0.9 at 560 nm ($OD_{560}$), IPTG was added at a final concentration of 0.5 mM. After 30 minutes, rifampycin was added (120 μg/ml) and incubation of the culture was continued for 75 minutes. The pellet of cells was kept at −70° C. until it was to be used. In order to purify p56, the cells were lysed with alumina in buffer A (50 mM Tris-HCl, pH 7.5, 1 mM ethylene diamine tetra-acetic acid (EDTA), 7 mM β-mercaptoethanol, 5% glycerol) containing 0.65 M NaCl. After eliminating the alumina and the cell residues by centrifugation, the lysate was incubated with polyethyleneimine (0.3%) for 20 minutes and, subsequently, it was centrifuged at 12,000 rpm in the Sorvall-GSA rotor for 10 minutes. The pellet was washed with buffer A containing 0.7 M of NaCl. Following centrifugation (12,000 rpm in the Sorvall-SS34 rotor for 20 minutes), successive precipitation steps with ammonium sulfate were performed (65%, 45% and 30% saturations, respectively). The supernatant of the last precipitation was taken to a final saturation of 50%. Following centrifugation, the pellet was re-suspended in buffer A, the salt concentration being 55 mM (estimated by conductivity). The protein preparation was loaded in a Mono Q column equilibrated with buffer A containing 55 mM NaCl. Protein p56 was eluted from the column with 0.3 M NaCl. Finally, the protein preparation was loaded in a glycerol gradient (from 15% to 30%) and centrifuged at 62,000 rpm in a Beckman-SW.65 rotor for 20 hours. The fractions containing protein p56 were collected and precipitated with 70% ammonium sulfate. Protein p56 was re-suspended in buffer A containing 50% glycerol and stored at −70° C.

1.5 Inhibition of UDG Activity Mediated by Protein p56
Detection of UDG Activity in *B. subtilis* Extracts In order to prepare the cell extracts, the *B. subtilis* 110NA strain (Moreno et al. (1974) Virology 62: 1-16) was grown in LB medium at 30° C. to an $OD_{560}$ equivalent to $10^8$ viable cells per ml of culture. Then, the culture was concentrated 10-fold in buffer U (50 mM Tris-HCl, pH 8.0, 200 mM NaCl, 12 mM β-mercaptoethanol, 1 mM EDTA) containing a mixture of protease inhibitors obtained from Roche Applied Science (a tablet of "Complete, Mini, EDTA-free" for 10 ml). The culture was lysed using the French press (20,000 psi) and, subsequently, the lysate was centrifuged at 7,000 rpm and 4° C. in the Sorvall-SS.34 rotor for 10 minutes. The supernatant (cell extract) was kept at 4° C. for a maximum period of two weeks. The total protein concentration in the extract (1.35 mg/ml) was calculated by Lowry's method.

Enzymes with UDG activity that belong to Family-1 eliminate uracil residues from both single-chain DNA and double-chain DNA. The elimination of the uracil residue generates a baseless site (AP site) in the DNA, which in *B. subtilis* is recognised and processed by protein ExoA. In the absence of an AP endonuclease activity, DNA chain splicing may be achieved in the AP site by treatment with NaOH and heat. In order to measure the UDG activity in the cell extract, a single-chain DNA (34 nucleotides) carrying a uracil residue in position 16 (ssDNA-$U^{16}$ substrate) was used. The nucleotide sequence of the ssDNA-$U^{16}$ polynucleotide is the following: 5'-CTGCAGGTGATGCGCUGTACCGATC-CCCGGGTAG-3' [SEQ ID NO: 8]. This DNA was radioactively labelled on the 5' end using [γ-$^{32}$P] ATP (3,000 Ci/mmol) (Amersham Pharmacia). The reaction mixture (20 µl) contained 0.55 ng of the ssDNA-$U^{16}$ substrate and the specified quantity of the cell extract (from 0.05 µg to 3.2 µg) in buffer U. The mixture was incubated at 37° C. for 10 minutes. Subsequently, it was treated with NaOH (0.2 M) and incubated at 90° C. for 30 minutes. The sample was analysed by electrophoresis in urea-containing (8 M) polyacrylamide gels (20%). The results obtained are shown in FIG. 1A.

In order to analyse whether protein p56 is an inhibitor of UDG activity, the ssDNA-$U^{16}$ substrate (0.55 ng) was incubated with 1.6 µg of the cell extract (a sufficient quantity to obtain total splicing of the substrate) and with different quantities of protein p56 (between 0.5 ng and 16 ng). As described above, the reaction mixtures were incubated at 37° C. for 10 minutes, treated with NaOH (0.2 M) and incubated at 90° C. for 30 minutes.

1.6 Interaction of Protein p56 with the UDG Enzyme

In order to analyse whether the UDG enzyme is a cellular target of protein p56, affinity chromatography assays were performed. Briefly, the *B. subtilis* 110NA [pPR53.p56FLAG] strain was grown in LB medium with phleomycin (0.8 µg/ml) at 30° C. to an $OD_{560}$ equivalent to $10^8$ viable cells per ml. The culture was concentrated 10-fold in TBS buffer (50 mM Tris-HCl, pH 7.5, 150 mM NaCl) and was lysed using the French press (20,000 psi). The lysate was centrifuged at 7,000 rpm and 4° C. in the Sorvall-SS.34 rotor for 10 minutes. The supernatant was loaded in an anti-FLAG M2 column (Sigma). The proteins bound to the column were eluted with the TBS buffer containing the FLAG peptide (500 µg/ml) (Sigma). The eluted proteins were precipitated with acetone, re-suspended in the loading buffer (60 mM Tris-HCl, pH 6.8, 2% SDS, 5% β-mercaptoethanol, 30% glycerol) and separated by electrophoresis in polyacrylamide/Tricine/SDS gels (Schagger and von Jagow (1987) Anal. Biochem. 166: 368-379). The gel was stained with SyproRuby (Molecular Probes). As a negative control, an extract from the 110NA [pPR53] strain was used. In a second experiment, protein p56 (2 µg) was incubated with the UDG enzyme of *E. coli* (0.2 µg, New England Biolabs). After 15 minutes at ambient temperature, the reaction was analysed by electrophoresis in native polyacrylamide gels (16%). The gel was stained with SpyroRuby.

II. Results 2.1 Protein p56 Interacts with the UDG Enzyme

Incubation of the substrate (ssDNA-$U^{16}$) with 0.2 µg of the cell extract of *B. subtilis* generated a splicing product. Moreover, the results show (FIG. 1A) that said substrate was completely spliced when 1.6 µg of the cell extract were used. The same splicing product was detected when the substrate was incubated with the UDG enzyme of *E. coli* (New England Biolabs). Therefore, the results show that the extract of *B. subtilis* was capable of eliminating the uracil residue from the substrate, generating an AP site, that is, said extract has UDG activity. However, under the conditions assayed (absence of $Mg^{2+}$), the extract of *B. subtilis* lacked AP endonuclease activity, since no splicing of the substrate was detected when the reaction mixtures were not treated with NaOH (FIG. 1A).

2.2. Protein p56 Inhibits UDG Activity

In order to prove that protein p56. is an inhibitor of UDG activity, the ssDNA-$U^{16}$ substrate (0.55 ng) was incubated with 1.6 µg of the cell extract (a sufficient quantity to obtain total splicing of the substrate) and with different quantities of protein p56 (between 0.5 ng and 16 ng). As already described in section 1.5 of Materials and Methods, the reaction mixtures were incubated at 37° C. for 10 minutes, treated with NaOH (0.2 M) and incubated at 90° C. for 30 minutes. FIG. 1B shows the results obtained. In the presence of 2 ng of protein p56, a decrease in the quantity of splicing product was detected. Moreover, the substrate remained intact when 8 ng of protein p56 were added. That is, the results show that protein p56 inhibits UDG activity.

Figure 2:
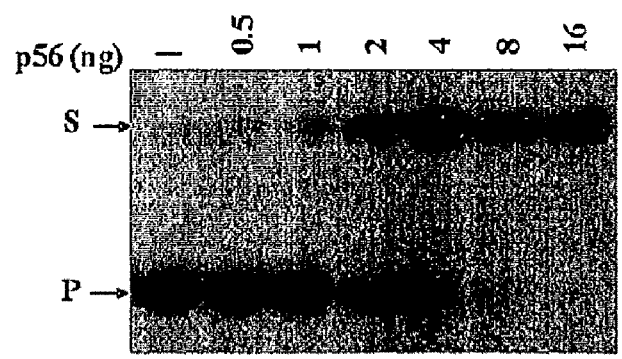
FIG. 2 shows the inhibition of the UDG activity of *B. subtilis* by protein p56. The specified quantity of p56 was added to 1.6 μg of extract. The reactions were treated with NaOH.
Figure 3:
FIG. 3 shows the co-elution of the UDG of *B. subtilis* with protein p56FLAG using anti-FLAG M2 columns (Sigma). The molecular mass (kDa) of the markers used is indicated on the right.
Figure 4:
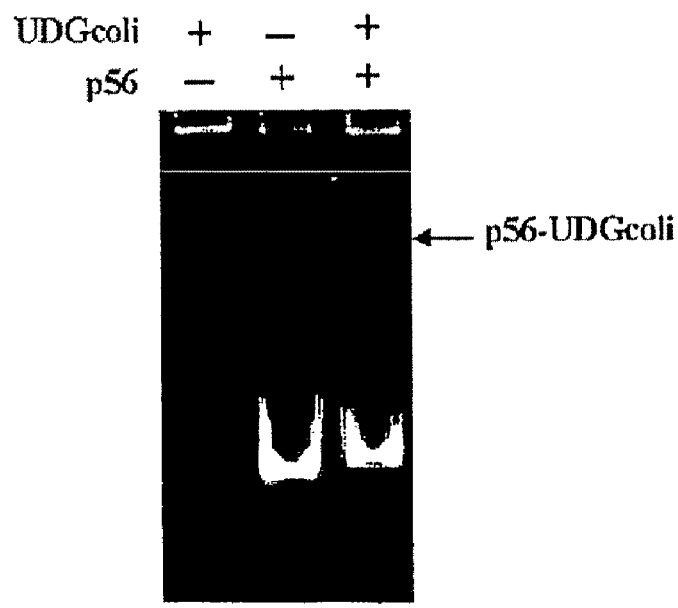
FIG. 4 shows the interaction of protein p56 with the UDG enzyme of *E. coli* analysed in a native polyacrylamide gel.

As shown in FIG. 2A, five proteins (A-E) co-eluted with p56FLAG. Using peptide mass fingerprinting and the MASCOT programme (Perkins et al. (1999) Electrophoresis 20: 3551-3567), protein D was identified to be the UDG enzyme (26 kDa). A band that moved faster than free UDG was detected (FIG. 2B). Using Western blot and peptide mass fingerprinting, it was confirmed that said band contained p56 and UDG.

The invention claimed is:

1. A method of treating a viral infection, comprising administering to a subject in need thereof a composition comprising: a therapeutically effective quantity of a protein comprising amino acid sequence SEQ ID NO: 1, and one or more pharmaceutically acceptable excipients.

* * * * *

SEQUENCE LISTING

<160> NUMBER OF SEQ ID NOS: 9

<210> SEQ ID NO 1

```
<211> LENGTH: 56
<212> TYPE: PRT
<213> ORGANISM: Artificial Sequence
<220> FEATURE:
<223> OTHER INFORMATION: synthetic protein

<400> SEQUENCE: 1

Met Val Gln Asn Asp Phe Val Asp Ser Tyr Asp Val Thr Met Leu Leu
1               5                   10                  15

Gln Asp Asp Gly Lys Gln Tyr Tyr Glu Tyr His Lys Gly Leu Ser
            20                  25                  30

Leu Ser Asp Phe Glu Val Leu Tyr Gly Asn Thr Ala Asp Glu Ile Ile
        35                  40                  45

Lys Leu Arg Leu Asp Lys Val Leu
    50                  55

<210> SEQ ID NO 2
<211> LENGTH: 171
<212> TYPE: DNA
<213> ORGANISM: Artificial Sequence
<220> FEATURE:
<223> OTHER INFORMATION: synthetic polynucleotide

<400> SEQUENCE: 2
atggtgcaaa atgattttgt tgactcatac gatgtgacaa tgttgcttca agatgatgac        60
ggtaaacagt attatgagta ccacaaggga ctgagtttgt cagactttga ggttctatac       120
ggtaacactg ctgatcaaat tataaaacta aggttggata aagtactatg a                171

<210> SEQ ID NO 3
<211> LENGTH: 26
<212> TYPE: DNA
<213> ORGANISM: Artificial Sequence
<220> FEATURE:
<223> OTHER INFORMATION: Primer oligonucleotide used for amplifying p56
      gene of bacteriophage phi-29

<400> SEQUENCE: 3
cgcattgtat gagctttcta ggatgg                                             26

<210> SEQ ID NO 4
<211> LENGTH: 31
<212> TYPE: DNA
<213> ORGANISM: Artificial Sequence
<220> FEATURE:
<223> OTHER INFORMATION: Primer oligonucleotide used for amplifying p56
      gene of bacteriophage phi-29

<400> SEQUENCE: 4
gcagggaatt ctgcagtcaa aggactttat c                                       31

<210> SEQ ID NO 5
<211> LENGTH: 20
<212> TYPE: DNA
<213> ORGANISM: Artificial Sequence
<220> FEATURE:
<223> OTHER INFORMATION: Primer oligonucleotide used for amplifying p56
      gene by PCR using pPR53.p56 plasmid as template

<400> SEQUENCE: 5
cctctagagt cgacctgcag                                                    20

<210> SEQ ID NO 6
<211> LENGTH: 41
<212> TYPE: DNA
<213> ORGANISM: Artificial Sequence
```

```
<220> FEATURE:
<223> OTHER INFORMATION: Primer oligonucleotide used for amplifying p56
      gene by PCR using pR53.p56 plasmid as template

<400> SEQUENCE: 6
gtcatcgtca tccttatagt caggacttta tccaaccta g                          41

<210> SEQ ID NO 7
<211> LENGTH: 45
<212> TYPE: DNA
<213> ORGANISM: Artificial Sequence
<220> FEATURE:
<223> OTHER INFORMATION: Primer oligonucleotide used for amplifying p56
      gene by PCR using 298 bp fragment of pPR53.p56 plasmid as template

<400> SEQUENCE: 7
ccctcagggc tgcagttatt acttgtcatc gtcatcctta tagtc                     45

<210> SEQ ID NO 8
<211> LENGTH: 34
<212> TYPE: DNA
<213> ORGANISM: Artificial Sequence
<220> FEATURE:
<223> OTHER INFORMATION: synthetic ssDNA-U substrate

<400> SEQUENCE: 8
ctgcaggtga tgcgctgtac cgatccccgg gtag                                 34

<210> SEQ ID NO 9
<211> LENGTH: 8
<212> TYPE: PRT
<213> ORGANISM: Artificial Sequence
<220> FEATURE:
<223> OTHER INFORMATION: synthetic FLAG peptide

<400> SEQUENCE: 9

Asp Tyr Lys Asp Asp Asp Asp Lys
1               5
```